United States Patent [19]

Fastaia et al.

[11] 4,160,373
[45] Jul. 10, 1979

[54] VEHICLE EXHAUST GAS ANALYSIS SYSTEM WITH GAS BLOCKAGE INTERLOCK

[75] Inventors: Anthony J. Fastaia, Vernon; Thomas A. Cross, Winsted, both of Conn.

[73] Assignee: United Technologies Corporation, Hartford, Conn.

[21] Appl. No.: 881,229

[22] Filed: Feb. 27, 1978

Related U.S. Application Data

[63] Continuation of Ser. No. 718,444, Aug. 26, 1976, abandoned, which is a continuation of Ser. No. 639,670, Dec. 13, 1975, abandoned, which is a continuation of Ser. No. 534,494, Dec. 19, 1974, abandoned.

[51] Int. Cl.² ............................................ G01N 21/26
[52] U.S. Cl. .................................................. 73/23; 340/608
[58] Field of Search ...................... 73/23, 27 R, 117.3, 73/117; 250/343, 344, 345; 340/607, 608, 632; 137/557

[56] References Cited

U.S. PATENT DOCUMENTS

| 2,761,037 | 8/1956 | Thomas | 340/607 |
| 3,406,562 | 10/1968 | Perna | 73/23 |
| 3,407,646 | 10/1968 | Traver | 73/23 |
| 3,593,023 | 7/1971 | Dodson et al. | 73/23 |
| 3,603,155 | 9/1971 | Morris | 73/23 |
| 3,630,072 | 12/1971 | Traver | 73/23 |
| 3,711,708 | 1/1973 | Dolin | 250/343 |
| 3,738,341 | 6/1973 | Loos | 73/23 |
| 3,768,084 | 10/1973 | Haynes | 340/607 |
| 3,790,798 | 2/1974 | Sternberg | 250/345 |
| 3,858,434 | 1/1975 | Hoppesch et al. | 73/23 |
| 3,860,344 | 1/1975 | Garfunkel | 250/345 |
| 3,938,377 | 2/1976 | Converse | 73/117.3 |

Primary Examiner—Stephen A. Kreitman
Attorney, Agent, or Firm—Donald F. Bradley

[57] ABSTRACT

The contaminants in the exhaust gas emissions from a motor vehicle such as carbon monoxide (CO) and hydrocarbons (HC) are analyzed within a nondispersive infrared analyzer which includes means for assuring that the vehicle being tested has achieved a predetermined engine speed and that no blockage has occurred in the gas transport system when the measurements are made.

1 Claim, 6 Drawing Figures

Fig 4a

VEHICLE EXHAUST GAS ANALYSIS SYSTEM WITH GAS BLOCKAGE INTERLOCK

This is a continuation of application Ser. No. 718,444 filed Aug. 26, 1976, which is a continuation of Ser. No. 639,670 filed Dec. 13, 1975, which is a continuation of Ser. No. 534,494 filed Dec. 19, 1974, now all abandoned.

CROSS REFERENCE TO RELATED APPLICATIONS

The disclosure herein, together with details of the full environment of this invention, are shown and described in Jowett, et al. copending application Ser. No. 534,495, filed on even date herewith and now U.S. Pat. No. 3,957,372.

BACKGROUND OF THE INVENTION

1. Field of the Invention

This invention relates to a system for automatically analyzing the contaminants in the exhaust gas emissions from a motor vehicle only when the exhaust gas input thereto is not blocked.

2. Description of the Prior Art

As a result of the increase in public concern over environmental pollution, governmental agencies and private citizens have joined in passing legislation which will limit the concentration of selected exhaust gas contaminants in the emissions from motor vehicles. A number of systems for measuring the concentration of contaminants in the exhaust gas emissions from motor vehicles have been developed. Many of the gas analysis systems do not have sufficient accuracy and do not produce consistent contaminant level readings. Many other exhaust gas analysis systems use analog outputs such as meters, most of which are nonlinear in their response and require continuous adjustment. Automated systems, however, can provide faulty results if the exhaust gas inputs thereto become blocked, which allows, willful false testing and/or erroneous indication of unnecessary repair.

SUMMARY OF THE INVENTION it is an object of the present invention to provide a system for measuring the concentration of selected contaminants in the exhaust gas emissions from a motor vehicle only when the gas input thereto is not blocked.

In accordance with a preferred embodiment of the present invention there is provided a gas analyzer and associated electronics to supply information as to the concentration of the selected contaminants in the exhaust gas only when pressure indications assure that the exhaust gas input to the analyzer is not blocked.

An error indication is also provided on the display unit if a blockage occurs in the gas feed to the infrared gas analyzer.

DESCRIPTION OF THE PREFERRED EMBODIMENT

Figure 1:
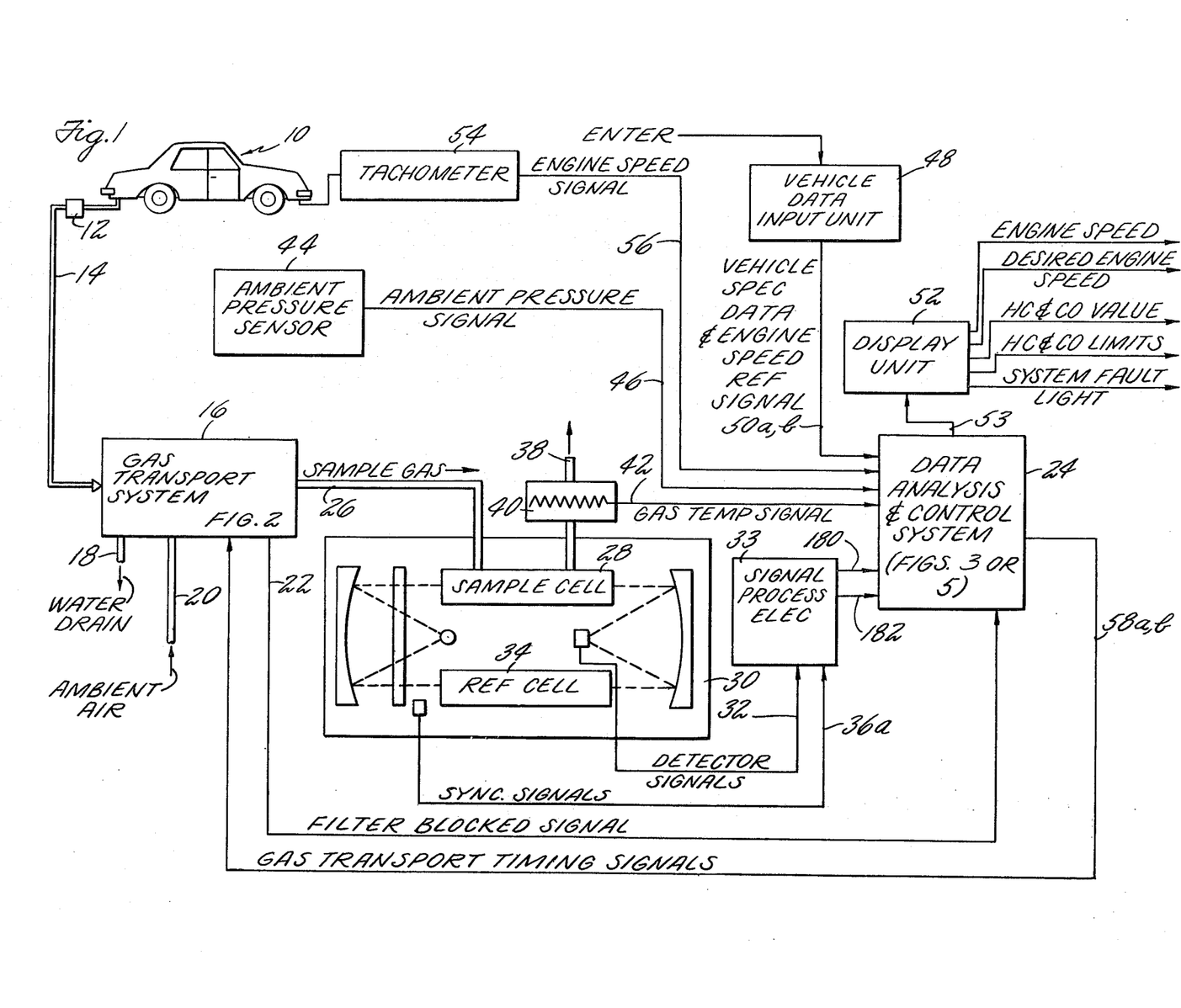
FIG. 1 is a schematic diagram partially in block diagram form of the vehicle exhaust gas analysis system connected to a vehicle and including an output display unit.

The basic vehicle exhaust gas analysis system is shown schematically in FIG. 1. A motor vehicle, shown as an automobile 10 and typically containing an internal combustion engine which emits exhaust gases containing pollutants, has attached to its exhaust emissions system, preferably at the tail pipe, an exhaust probe 12 which is designed so that it will not slip out of the vehicle's tail pipe under both normal vehicle vibrations and full load engine vibrations. A hand grip may be provided as part of the probe, and the probe should be flexible enough to extend into a curved tail pipe at least six inches if possible. For automobiles having dual exhausts two probes are required.

Attached to the probe 12 is a flexible gas transmission line which is preferably in the form of a hose 14 which serves as a link between the tail pipe probe 12 and a gas transport system 16. The hose 14 is preferably oil resistant and constructed of an internal hose material which will withstand high concentrations of gases without inducing hang up of the gases within the hose. Provisions may be made for storage of the hose 14 when not in use. The hose should also be able to withstand the abuse of being driven over a heavy vehicle and return to its original shape and cross-sectional area within a short time. The hose 14 should be able to withstand tail pipe gas temperatures up to 200° F. and have an inside diameter such as to permit purging of its entire length within a few seconds.

Figure 2:
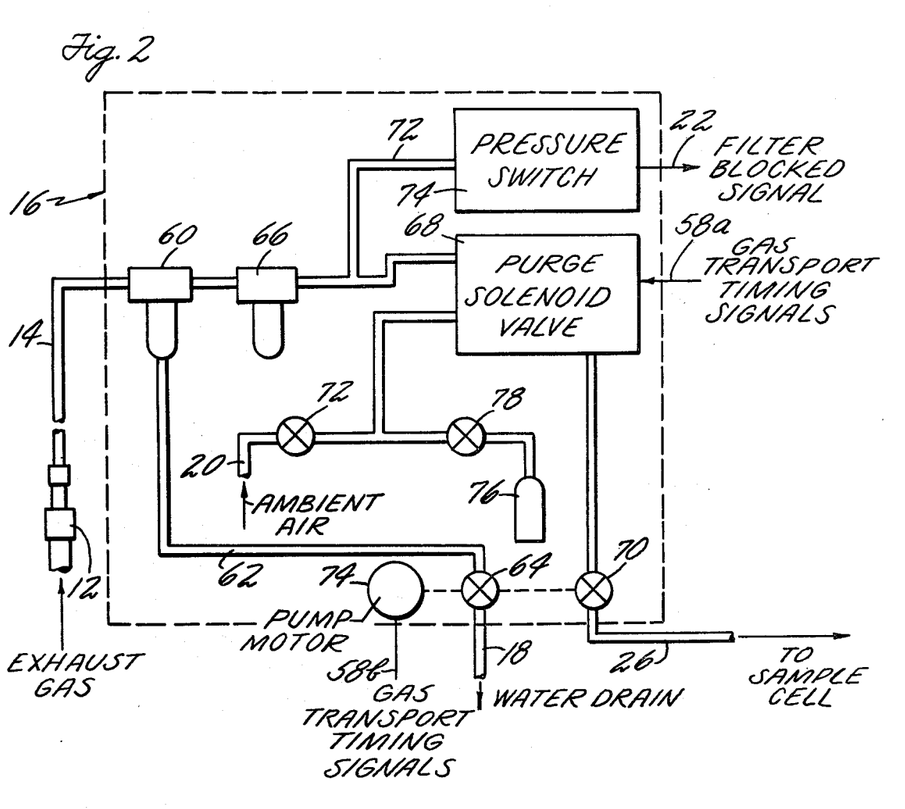
FIG. 2 is a schematic diagram of the gas transport system of FIG. 1.

As is explained in detail in conjunction with FIG. 2, the gas transport system 16 contains replaceable particulate filters, a water removal system wherein water in the exhaust gas is eliminated through a water drain 18, a pumping system including a pump motor for pumping the gas to be analyzed to a nondispersive infrared gas analyzer, and a solenoid operated gas purge system which purges the system of exhaust gas and replaces it with ambient air from an inlet 20. In accordance with the invention, the gas transport system 16 also contains a pressure switch, shown more particularly in conjunction with FIG. 2, which senses pressure to determine if a blockage has occurred in the gas transport system. A filter blocked signal is fed to a data analysis system 24 via a signal line 22 if a pressure loss in the gas transport system 16 is sensed.

The sample gas, either filtered exhaust emissions from the vehicle or ambient air, is fed from the gas transport system 16 through a gas line 26 into a sample cell 28, the sample cell being contained within a nondispersive infrared gas analyzer 30. Briefly, the nondispersive infrared gas analyzer 30 passes a beam of infrared radiation through the sample cell 28 into which the sample gas has been pumped. Two detectors, each having a separate light filter which blocks all but the wavelengths of interest, respond to the absorption of infrared radiation by the particular component of gas within the sample cell 28 which falls within the selected wavelengths passed by the filters, the electronic signals from the detector being fed via lines 32 into a signal processing electronics system 33. The nondispersive infrared gas analyzer 30 also contains a reference cell 34 which is fully or partially sealed and which contains a reference gas, the infrared absorption of which is compared to that in the sample cell 28. Synchronization is provided by photosensitive devices which provide synchronizing signals via lines 36 to the signal processing electronics 33. After processing, the electronic signals are fed from the signal processing electronics 33 to a data analysis system 24 via lines 180 and 182.

After the sample gas has been analyzed in the nondispersive infrared gas analyzer 30, it is removed from the sample cell 28 through a vent 38. Positioned within the vent 38 is a thermistor 40 which measures the temperature of the exhaust gas from the sample cell 28 and provides a signal indicative of gas temperature via line 42 to the data analysis system 24.

Since the absorption of infrared light within the sample cell is affected not only by the temperature of the gas within the sample cell 28 but by the ambient pressure, an ambient pressure sensor 44, which may be a simple pressure transucer, produces an ambient pressure signal which is fed to the data analysis system 24 via a signal line 46.

The concentration of more than one gas component may be measured simultaneously in the nondispersive infrared gas analyzer 30 by positioning a plurality of detectors with appropriate filters in the path of the infrared beam which has passed through the sample cell 28 and the reference cell 34. Typical contaminants specified by federal and state regulations at this time are carbon monoxide (CO) and a hydrocarbon component (HC), typically hexane. Regulations also specify various limits in the amount of CO and HC in the vehicle exhaust gases at various engine speeds and under specified load conditions. The present system is adapted to measure and display the amount of the selected emission contaminants in the vehicle exhaust gas under any of a number of specified test conditions. In a typical gas emission testing installation, the system operator will determine from the type of vehicle under test the particular test conditions which may be specified by local law, and the limits for CO, HC and/or other contaminants which may be specified by law. In a typical installation the operator will determine the appropriate vehicle specification data from tables (including speed and load conditions and HC and CO limits) and enter the data into a vehicle data input unit 48 which provides appropriate signals as to the specific vehicle data to the data analysis system 24 via lines 50. In more sophisticated systems which may include automotive diagnostic systems, the appropriate vehicle specification data may be stored in a memory unit and the operator merely enters the appropriate vehicle identification code into the vehicle specification data input unit 48, the appropriate vehicle specification data being automatically supplied to the data analysis system 24. Although not shown, the vehicle specification data on lines 50 may also be fed directly to a display unit 52 for display, preferably in digital form, for use by the operator.

The display unit 52 receives data from the data analysis system 24 via lines 53. The display unit 52 may be a hand held controller which is used by the operator during the emissions testing, the hand held controller being of the type disclosed and claimed in U.S. Pat. No. 4,113,980.

The display unit 52 may, either automatically or under the control of the operator, display any of the information which may be useful for conducting the emissions analysis testing. For example, the display unit may display the desired engine speed for the emissions test. At this time the operator causes the vehicle 10 to achieve the desired engine speed such as by depressing the vehicle accelerator pedal. A tachometer 54 may be connected to the vehicle 10 in a known manner to produce a signal indicative of engine speed, which is fed via a line 56 to the data analysis system 24 and which also may be displayed by the display unit 52. Although not shown, a dynamometer may be used to provide appropriate loading to the drive wheels of the vehicle, a signal indicative of vehicle load also being fed to the data analysis system 24. With desired engine speed and actual engine speed being displayed to the operator by display unit 52, the operator has a positive indication when the engine speed achieves the desired engine test speed. Once the vehicle has acheived the desired test speed for a sufficient time for the sample cell 28 to contain a representative exhaust gas sample, the emissions analysis may be performed and the measured CO and HC values displayed by display unit 52. The display unit 52 may also display, either automatically or at the request of the operator, the CO and HC limits so that it can easily be determined whether or not the vehicle meets the standards. The display unit 52 may also contain one or more indicator lights which automatically indicate a system fault, such as a blockage in the gas transport system 16 according to the invention or a deviation from the desired engine speed.

The data analysis system 24 may be an analog processor, but preferably is a suitably programmed multipurpose digital computer of the type well known to those skilled in the art. The function of the data analysis system 24 is to compute the CO and HC values in a manner to be described from the various input data, to control the operation and timing of the gas transport system 16 by means of gas transport timing signals fed via lines 58a, b and to feed the desired data to display unit 52 via line 53. Examples of both analog and digital units for performing the desired functions will be described subsequently, the digital unit being shown in FIG. 3 and the analog unit in FIG. 5.

FIG. 2 shows in detail the gas transport system 16 of FIG. 1. The exhaust gas from the vehicle under test is fed through the tail pipe probe 12 and the hose 14 into a filtering system which consists of a coarse filter and water separator 60. The filter 60 is typically a 25 micron filter. Any water in the exhaust gas is separated out and fed from the filter 60 through a drain line 62 which contains a pump 64, the separated water ultimately being drained from the system via an outlet 18. After coarse filtration, the exhaust gas proceeds from the filter 60 to a fine filter 66 which is typically a 0.6 micron filter. Upon exiting from the fine filter 66, the filtered exhaust gas passes through a purge solenoid valve 68, and then through a pump 70 where the gas passes from the exhaust gas transport system 16 via the line 26 into the sample cell 28, which is contained within the nondispersive infrared gas analyzer 30.

According to the invention, there is provided in the line between the fine filter 66 and the purge solenoid valve 68, a pressure sensitive switch 74 which measures the adequacy of gas flow through the filters 60 and 66 by sensing the pressure drop across the filters via line 72. The pressure switch is referenced to ambient air and is typically set to close and produce a filter blocked signal via line 22 when the pressure drop across the filters increases to between 6 and 8 inches of mercury. Typically, a reduced pressure on line 72 is indicative of blockage in the filters, but can also be caused by the twisting of or an obstruction in the tail pipe probe 12 or hose 14. In any case, the generation of a filter blocked signal on the line 22 and the display thereof by a display light in display unit 52 of FIG. 1 is indicative of some malfunction in the gas transport system requiring action by the operator. Cleaning or replacement of the filters 60 or 66 is a typical solution to an excessive pressure drop.

The purge solenoid valve 68 is a two-way valve which provides a gas input via the pump 70 to the sample cell 28. In one position, the solenoid valve permits passage therethrough of the exhaust gas from the vehicle under test. In the other position the purge solenoid valve 68 blocks the exhaust gas line and causes ambient air from the input gas line 20 to pass through a normally open valve 72, through the purge solenoid valve 68, and into the sample cell 28 via the pump 70. The position of the purge solenoid valve 68 is determined by the gas transport timing signal on the line 58a, which is provided by the data analysis system 24 of FIG. 1. Operation of the gas analysis system requires that the sample cell initially be purged and contain ambient air, at which time a measurement is taken, by infrared techniques, of the magnitude of the selected contaminants in the ambient air within the sample cell. After the ambient air reading has been taken, the purge solenoid valve 68 is actuated via a signal on the line 58a to block the ambient air input and to permit the exhaust gas from the vehicle under test to fill the sample cell 28, at which time another reading of the contaminants contained in the gas in the sample cell is taken. After this latter reading, the purge solenoid valve 68 is again actuated to shut off the exhaust gas and to admit ambient air to purge the sample cell 28. Exhaust gas is admitted to the sample cell 28 only for the time necessary to obtain the desired data and is then immediately purged, in order to prevent contamination of the sample cell 28 by the impurities in the exhaust gas.

The pump 64, which purges water from the coarse filter 60, and the pump 70, which pumps either the exhaust gas or ambient air into the sample cell 28, are both controlled by a single pump motor 74 which responds to the gas transport timing signals on the line 58b. The pump motor 74 may be turned off to conserve power between tests.

The flow rate of pump 64 should be sufficient to insure that the water extracted from the exhaust emissions during testing of a vehicle will not accumulate in the filter 60, but should be sufficiently less than the flow of pump 70 to insure that adequate exhaust gas will flow from the exhaust gas probe 12 into the sample cell 28. For most efficient operation, the flow rate of the pump 70 should be such as to insure that an adequate sample of exhaust gas from the vehicle under test fills the sample cell in a few seconds. The source of ambient air 20 should be located such as to assure that the ambient air admitted to the system is not contaminated by exhaust emissions.

For initial calibration of the exhaust emissions analysis system, and for calibration at selected intervals during operation, a sample gas, such as pure nitrogen or a gas containing known amounts of selected contaminants as provided by a container 76, is connected to the purge solenoid 68 through normally closed valve 78. When it is desired to calibrate the system, valve 72 is closed and valve 78 is opened and the calibration gas in container 76 is pumped into the sample cell 28. Calibration is performed by adjusting the signal conditioning electronics 33 as is described hereinafter.

The heart of the exhaust emissions analysis system is the nondispersive infrared gas analyzer 30 and its associated components described in detail in the aforementioned Jowett, et al. patent. Briefly, a source of infrared radiation of the desired wavelength is passed alternately through the closed reference cell 34 containing a reference gas such as clean air, and then through the gas sample cell 28 which contains either ambient air or the exhaust gas from the vehicle. The infrared radiation, after passing either through the reference cell or the gas sample cell, is focused through a suitable infrared filter onto a detector which produces electrical signals which will vary as a function of the absorption of light in the desired wavelength band by the selected gas component contained in each of the cells. After conditioning by suitable electronics, the output signals from the detector are used to calculate the concentration of the selected gas component. By placing two or more detectors with suitable filters in the same infrared radiation path, the concentration of two or more gas components can be measured simultaneously with a single gas analyzer.

Figure 3:
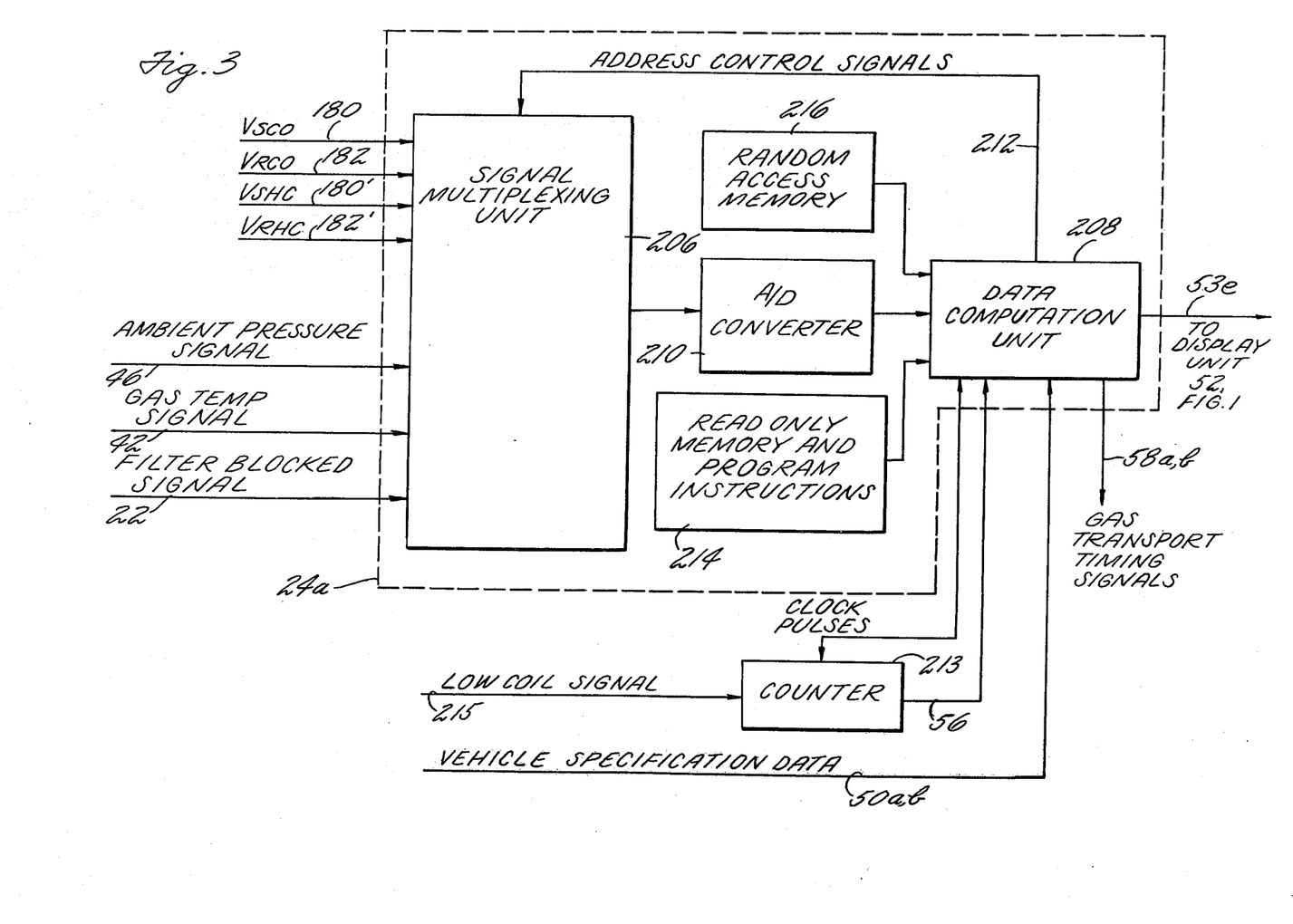
FIG. 3 is a schematic block diagram of a digital embodiment of the data analysis and control system of FIG. 1.

FIG. 3 shows a preferred embodiment of the emissions analysis system in which the computations and corrections are performed by a digital data analysis system 24a which includes a digital data computation unit 208. The digital computation unit 208 may be a general purpose digital computer. A flow chart illustrating representative program steps performed by the digital data computation unit 208 is described in FIGS. 4a and 4b.

FIG. 3 contains a signal multiplexing unit 206. Feeding into the signal multiplexing unit 206 are the output signals $V_{SCO}$, $V_{RCO}$, $V_{SHC}$ and $V_{RHC}$ on lines 180, 182, 180' and 182', respectively. Also fed into the signal multiplexing unit 206 are the filter blocked signal on the signal line 22, the gas temperature signal on the signal line 42, and the ambient pressure signal on the signal line 46.

The signal multiplexing unit 206 receives each of the analog input signals and feeds the selected signal at the proper time to data computation unit 208 through an analog-to-digital converter 210 under the control of the address control signals appearing on line 212.

Also fed directly to the data computation unit 208 are the vehicle specification data signals on lines 50a,b and the engine speed signal on signal line 56. The engine speed signal may be generated as shown in FIG. 1 by means of a tachometer, or a counter 213 may be used as shown in FIG. 3 to generate a signal on line 56 which is proportional to engine speed. Fed to the counter 213 are clock pulses from a source, not shown, within data computation unit 208, and a series of timing pulses from the low coil of the vehicle under test on a line 215. The counter 213 is adapted to be actuated by a selected low coil pulse, and stopped by the next low coil pulse, the number of clock pulses counted therein between coil pulses being proportional to engine speed. For example, if the vehicle under test has an 8 cylinder engine, the time between two low coil pulses is equal to ¼ revolution of the engine, or 90°. The data computation unit 208 receives the count from counter 213 on line 56 and computes the engine speed therefrom, the computation being a function of the number of engine cylinders, which data has been fed to the data computation unit via lines 50a,b with the vehicle specification data.

The data computation unit 208 as previously indicated may be a general purpose digital computer. The program instructions and necessary additional data such as constants are stored in a read only memory 214 which controls the operation of the data computation unit 208. Temporary storage during computation is provided by a random access memory 216 which is in communication with the data computation unit 208. The outputs from the data computation unit 208 include an input to the display unit 52 via output line 53e and the generation of gas transport timing signals on signal lines 58a,b, the latter signals being fed to the exhaust gas transport system 16 described in detail in FIG. 2 and which signals control the actuation of the purge solenoid valve 68 and the actuation of pump motor 74 to cause either ambient air or exhaust gas to fill the sample tube 28 at the proper times.

Figure 4A:
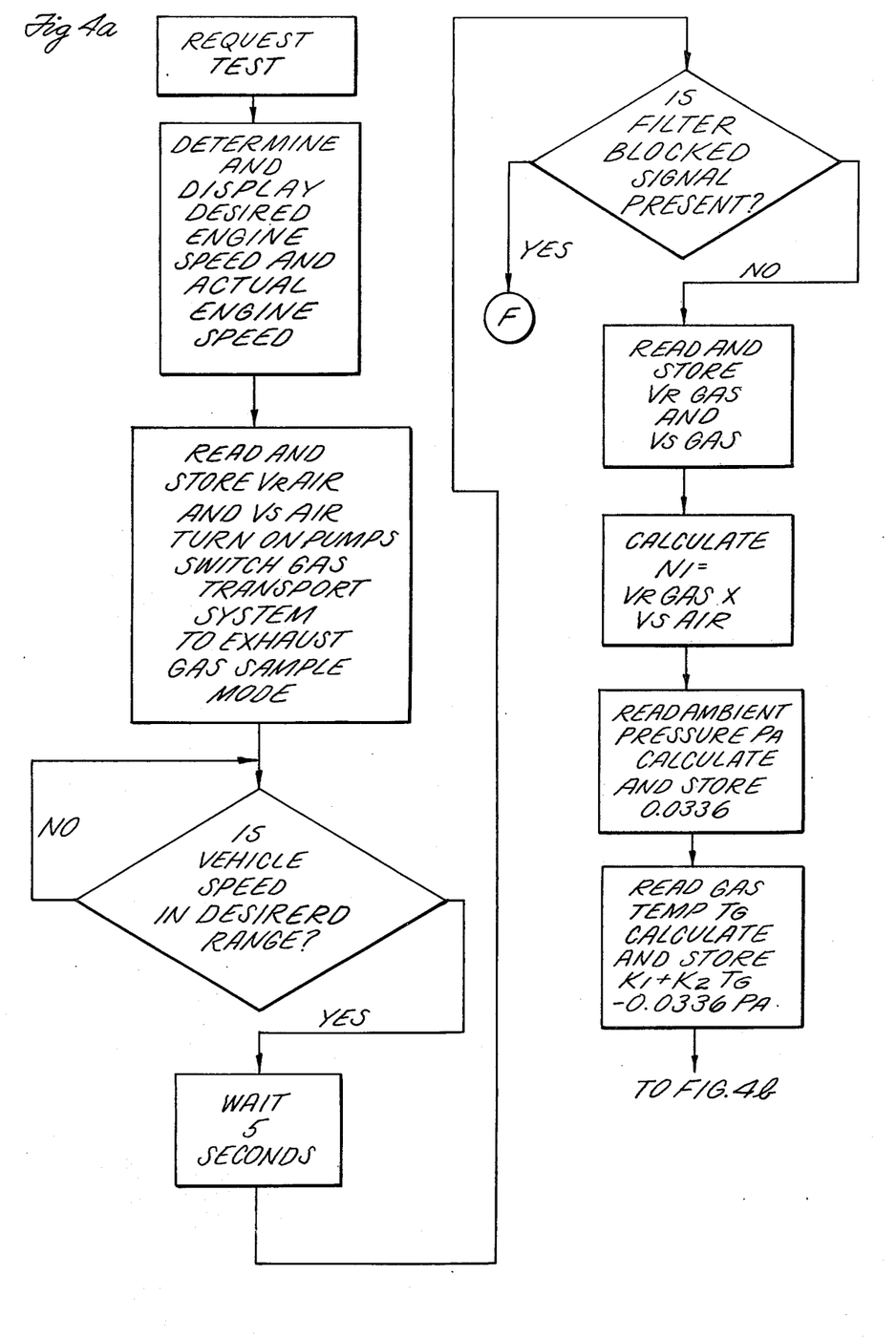
FIGS. 4a and 4b are a flow chart of the program instructions for the digital computation unit of FIG. 3.
Figure 4B:
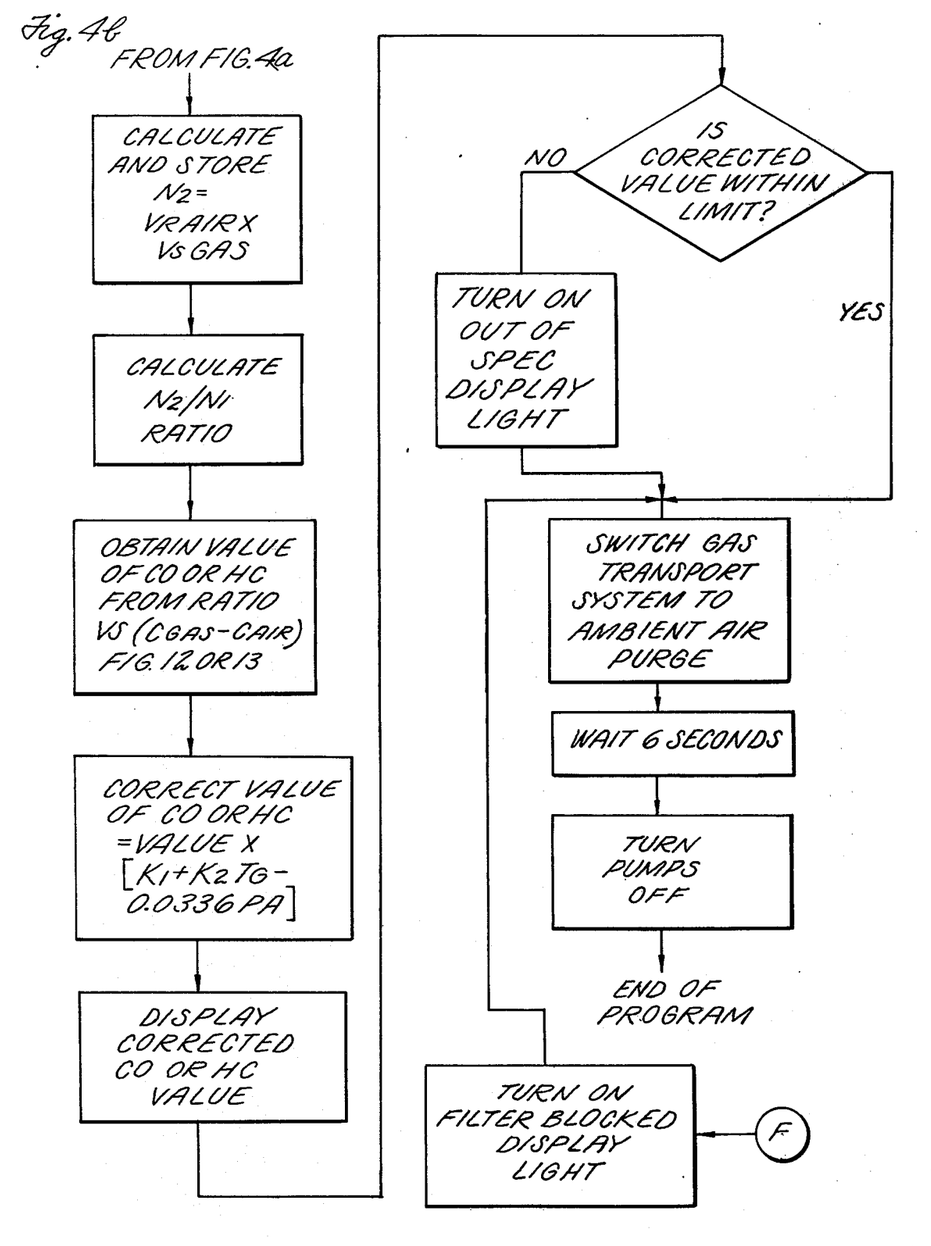

The data computation unit 208 of FIG. 3 accepts the signals from the signal multiplexing unit 206, performs the computation as is shown by the flow chart in FIG. 4, and corrects the calculated ratio for nonlinearities, and for ambient pressure and gas temperature.

FIGS. 4a and 4b are simplified flow chart showing representative program steps which may be contained in the program instructions stored in random access memory 214 of FIG. 3 and which control the computations in data computation unit 208 and the transmission of the input signals from the signal multiplexing unit 206 to the analog-to-digital converter 210 and then to the data computation unit 208. The outputs from the data computation unit 208 to the display unit 52 via line 53e and the initiation of the gas transport timing signals on lines 58a,b are also controlled by the program steps shown in FIGS. 4a and 4b. It will be apparent to one skilled in the art of digital computer programming that various other program steps and implementations of the invention may be performed depending on the specific construction and operation of the data computation unit 208.

Although not shown in the flow chart of FIGS. 4a and 4b, the engine speed may be continuously monitored, i.e., compared with the desired vehicle engine speed illustrated as the engine speed reference signal in conjunction with the vehicle specification data on lines 50a,b of FIG. 1. If the actual engine speed is out of the desired range, i.e., a range centered about the desired engine speed, the HC and CO values are not displayed in display unit 52 and an indicator light in display unit 52 may be turned on, indicating that the engine speed must be adjusted. The filter blocked signal on the line 22 may also be continuously monitored, and if present the computations terminated and the system purged with ambient air. The manner of implementation of these program steps may be in accordance with programming techniques which are well known to those skilled in the art and are therefore not described in detail.

If desired the $V_{R\ GAS}$ and $V_{S\ GAS}$ signals may be continuously monitored during the time that these readings are made, new $V_{R\ GAS}$ and $V_{S\ GAS}$ signals being taken approximately twice per second. The computations of the HC and CO values may also be continuously updated in like manner, and averaged on a continuous basis so that the values displayed in display unit 52 are the average values of HC and CO. Other changes in the program steps will be apparent to those skilled in the art.

Figure 5:
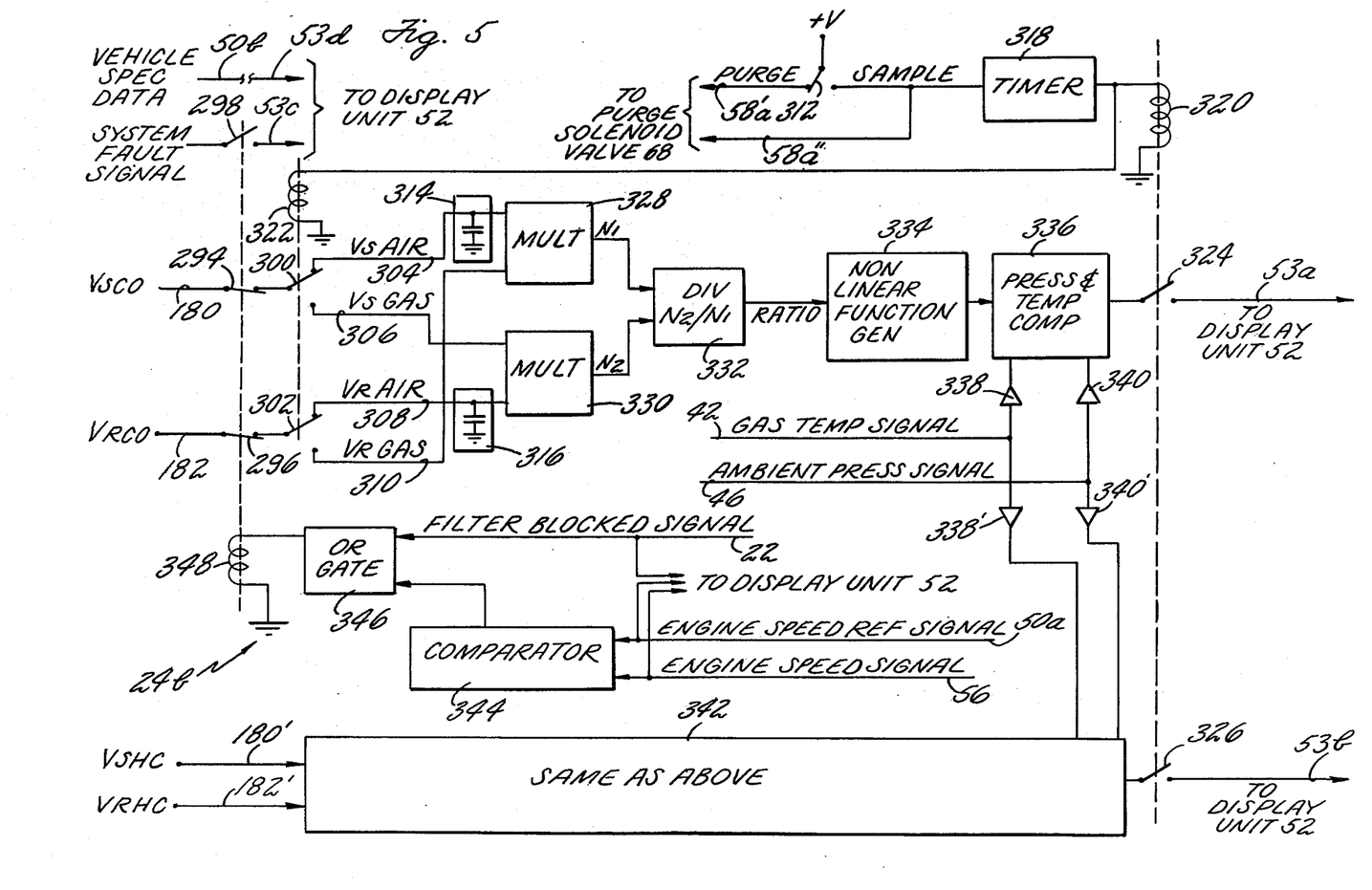
FIG. 5 is a schematic diagram of an analog implementation of the data analysis and control system of FIG. 1.

An analog implementation of the system of this invention is shown in FIG. 5. The various input signals in FIG. 1 are fed to an analog data analysis system 24b and which is equivalent to the digital data analysis system 24a of FIG. 3. Referring to the FIG. 5, the $V_{SCO}$ and $V_{RCO}$ signals appearing on signal lines 180 and 182 are fed respectively through normally closed switches 294 and 296, whose operation will be described subsequently, and then through switches 300 and 302 respectively, the $V_S$ signal being fed to lines 304 or 306 labeled $V_{S\ AIR}$ and $V_{S\ GAS}$ respectively depending on the position of switch 300, and the $V_R$ signal being fed to lines 308 or 310 which are labeled $V_{R\ AIR}$ and $V_{R\ GAS}$ respectively, depending on the position of switch 302. The position of switches 300 and 302 is determined by the position of switch 312 which is actuated manually by the operator of the system. Switch 312 has two positions, PURGE and SAMPLE, and is biased so that unless it is held by the operator in the SAMPLE position, it will return to the PURGE position. Switch 312 may be a time delay switch which returns to the PURGE position after a selected time such as eight seconds after being moved to the SAMPLE position. While in the PURGE position, a signal is fed via line 58a' to purge solenoid 68 to cause the purge solenoid to admit ambient air into the sample cell. While switch 312 is in the PURGE position, the switches 300 and 302 are normally biased as shown in FIG. 5, i.e., in contact with lines 304 and 308 respectively.

Assuming that switch 312 is in the PURGE position, the $V_{S\ AIR}$ signal on line 304 is fed to a sample and hold circuit 314 where the $V_{S\ AIR}$ signal is stored. Likewise the $V_{R\ AIR}$ signal on line 308 is fed to a sample and hold circuit 316 where it is stored.

When a vehicle is ready to be tested, and has reached the desired test speed as shown by an indication on the display unit 52, the operator moves switch 312 to the SAMPLE position. At this time a signal is fed via line 58a'' to the purge solenoid valve 68 to cause the ambient air inlet to be blocked and exhaust gas to be admitted to the sample cell 28. A timer 318 is also actuated, and after a suitable time such as seven seconds to assure that the sample tube is filled with exhaust gas, the timer 318 times out causing relays 320 and 322 to be actuated. Actuation of relay 320 closes normally open switches 324 and 326 whose operation will be described subsequently, the actuation of relay 322 moves switches 300 and 302 to feed the $V_{SCO}$ and $V_{RCO}$ signals on lines 180 and 182 to lines 306 and 310 respectively.

Connected to the output from sample and hold circuit 314 and also receiving the signal on line 308 is a multiplier 328 which generates the product $N_1 = V_{S\ AIR} \times V_{R\ GAS}$. Connected to the output from sample and hold circuit 316 and also receiving the signal on line 306 is a multiplier 330 which generates the product $N_2 = V_{S\ GAS} \times V_{R\ AIR}$. The $N_1$ and $N_2$ outputs from multipliers 328 and 330 are fed to a divider 332 where the division $N_2/N_1$ is effected. The RATIO signal from divider 332 is fed to a nonlinear function generator 334 where the compensation to the RATIO signal for temperature and pressure, in accordance with the aforementioned Jowett, et al. patent, is performed. Function generator 334 may be a simple diode network. The output from the nonlinear function generator 334 is then fed to pressure and temperature compensator 336 where the computed value of CO is compensated for pressure and temperature. To accomplish this compensation, the gas temperature signal on line 42 and the ambient pressure signal on line 46 are fed respectively through scaling amplifiers 338 and 340 into compensator 336, which are then summed in a summing junction (in compensator 336) with a fixed signal representing a constant. The output of the summing junction is multiplied with the output of the function generator 334 in an analog multiplier (in the compensator 336).

The output from compensator 336 is the resultant CO measurement signal which is then fed through switch 324, now closed because of actuation off relay 320, and via line 53a to display unit 52. Once the CO measurement is made and displayed on display unit 52, the operator moves switch 312 back to PURGE, or switch 312 will move back to PURGE after a selected time delay, thereby opening switch 324 so that no signal can thereafter pass therethrough.

The HC measurements are made by analog apparatus 342 which is identical to that just described (except for the nonlinear function, which is different) and which receives inputs $V_{SHC}$ via line 180' and $V_{RHC}$ via line 182', and also receives temperature and pressure input signals via scaling amplifiers 338' and 340'. The computed HC signals is fed via switch 326 and line 53b to display unit 52 at the same time that the CO signal is fed to the display unit.

If, during the measurements, the engine speed on line 56 deviates from the engine speed reference signal on line 50a by an amount determined within a comparator 344, or if, in accordance with the invention, a filter blocked signal appears on line 22, OR gate 346 is actuated and relay 348 is energized to open switches 294 and 296 so that a zero output signal is produced on lines 53a and 53b, and switch 298 is closed to cause a system fault signal to be passed to display unit 52 via line 53c.

Vehicle specification data in this embodiment which appears on line 50b may be fed directly to display unit 52 via line 53d.

While the invention has been described with respect to preferred embodiments thereof, it will be apparent to those skilled in the art that changes and modifications may be made to the construction and arrangement of parts and the operation thereof without departing from the scope of the invention as hereinafter claimed.

We claim:

1. An engine exhaust gas analysis system for measuring the amount of a selected contaminant contained within a sample of engine exhaust gas comprising:
   a gas sample cell adapted to contain a gas;
   a reference cell containing a reference gas;
   means including a gas transport system for filling said sample cell with a sample of exhaust gas;
   sampling means associated with said cells for producing electrical signals related to the concentration of the selected contaminant within the sample of gas;
   pressure means connected to said gas transport system and responsive to the pressure of gas therein to generate a blockage signal alternatively indicative of whether or not said gas pressure is in excess of a preselected pressure below which blockage of said gas transport is to be presumed; and
   a data analysis and control system responsive to said sampling means and to said pressure means, for receiving said electrical signals and calculating therefrom the concentration of the selected gas contaminant and providing an output signals indicative thereof, only in concurrence with said blockage signal indicating the pressure in said gas transport system being in excess of said preselected magnitude.

* * * * *